US009695461B2

(12) United States Patent
Siegert et al.

(10) Patent No.: US 9,695,461 B2
(45) Date of Patent: Jul. 4, 2017

(54) METHOD FOR ADAPTING A HYDROLYTIC ENZYME TO A COMPONENT THAT STABILIZES THE HYDROLYTIC ENZYME

(71) Applicant: Henkel AG & Co. KGaA, Duesseldorf (DE)

(72) Inventors: Petra Siegert, Haan (DE); Stefan Evers, Haan (DE); Marion Merkel, Cologne (DE); Nina Mussmann, Willich (DE); Hendrik Hellmuth, Duesseldorf (DE); Timothy O'Connell, Duesseldorf (DE); Karl-Heinz Maurer, Erkrath (DE); Ulrich Schwaneberg, Kelmis-Hergenrath (BE); Felix Jakob, Erkelenz (DE); Ronny Martinez, Aachen (DE); Brian Laufs, Juechen (DE); Ayhan Aydemir, Duesseldorf (DE); Thomas Weber, Dormagen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/199,569

(22) Filed: Mar. 6, 2014

(65) Prior Publication Data

US 2014/0186868 A1 Jul. 3, 2014

Related U.S. Application Data

(63) Continuation of application No. PCT/EP2012/066237, filed on Aug. 21, 2012.

(30) Foreign Application Priority Data

Sep. 12, 2011 (DE) .......................... 10 2011 118 027

(51) Int. Cl.
| | | |
|---|---|---|
| *A01N 25/30* | (2006.01) | |
| *C12N 9/54* | (2006.01) | |
| *C12Q 1/37* | (2006.01) | |
| *C11D 3/386* | (2006.01) | |
| *C12N 9/96* | (2006.01) | |

(52) U.S. Cl.
CPC ............ *C12Q 1/37* (2013.01); *C11D 3/38663* (2013.01); *C11D 3/38681* (2013.01); *C12N 9/54* (2013.01); *C12N 9/96* (2013.01)

(58) Field of Classification Search
CPC combination set(s) only.
See application file for complete search history.

(56) References Cited

U.S. PATENT DOCUMENTS

| | | | |
|---|---|---|---|
| 7,300,782 | B2 | 11/2007 | Breves et al. |
| 2004/0259222 | A1 | 12/2004 | Breves et al. |
| 2009/0170745 | A1 | 7/2009 | Merkel et al. |
| 2009/0275493 | A1 | 11/2009 | Siegert et al. |
| 2012/0171754 | A1 | 7/2012 | Bessler et al. |

FOREIGN PATENT DOCUMENTS

| | | |
|---|---|---|
| EP | 0478050 A1 | 4/1992 |
| EP | 0511456 A1 | 11/1992 |
| EP | 0832174 B1 | 5/2002 |
| GB | 1243784 | 8/1971 |
| WO | 91/02792 A1 | 3/1991 |
| WO | 92/19707 A1 | 11/1992 |
| WO | 93/18140 A1 | 9/1993 |
| WO | 96/21716 A1 | 7/1996 |
| WO | 96/34946 A1 | 11/1996 |
| WO | 96/41859 A1 | 12/1996 |
| WO | 98/23732 A2 | 6/1998 |
| WO | 00/60060 A2 | 10/2000 |
| WO | 01/44452 A1 | 6/2001 |
| WO | 02/29024 A1 | 4/2002 |
| WO | 03/057246 A1 | 7/2003 |
| WO | 2005/118793 A2 | 12/2005 |
| WO | 2007/079938 A2 | 7/2007 |
| WO | 2008/002472 A2 | 1/2008 |
| WO | 2008/007319 A2 | 1/2008 |

OTHER PUBLICATIONS

Probing the Specificity of the Si Binding Site of M222 Mutants of Subtilisin B. Lentus With Boronic Acid Inhibitors. Michele R. Stabile, Bioorganic & Medicinal Chemistry Letters. vol. 6, No. 21, pp. 2501-2506, 1996.*
PCT International Search Report (PCT/EP2012/066237) dated Mar. 12, 2012.
Michaelis et al., "Die Kinetik der Invertinwirkung", Biochem. Z., 49, 333-369, 1913, English translation by Roger S. Goody and Kenneth A. Johnson.
Gornall et al., "Determination of Serum Proteins by Means of the Biuret Reaction", Journal of Biological Chemistry, vol. 177, pp. 751-766, 1948.
Van Raay et al, "The Determination of Proteolytic Activity in Enzyme Concentrates and Enzyme Containing Detergents", Tenside Detergents, vol. 7, No. 3, pp. 125-132, 1970.
Cheng et al., "Relationship Between the Inhibition Constant (KI) and the Concentration of Inhibitor which Causes 50 Per Cent Inhibition (I50) of an Enzymatic Reation", Biochemical Pharmacology, vol. 22, pp. 3099-3108, 1973.
Delmar et al., "A Sensitive New Substrate for Chymotrypsin", Analytical Biochemistry, vol. 99, pp. 316-320, 1979.
Altschul et al., "Basic Local Alignment Search Tool", Journal of Molecular Biology, vol. 215, pp. 403-410, 1990.

(Continued)

*Primary Examiner* — Kagnew H Gebreyesus
(74) *Attorney, Agent, or Firm* — Thomas G. Krivulka

(57) ABSTRACT

The stabilization of a hydrolytic enzyme in a liquid preparation is to be improved through a component that stabilizes the hydrolytic enzyme. This is accomplished by a method for adapting a hydrolytic enzyme to a component that stabilizes the hydrolytic enzyme, comprising the following method steps: a) providing a hydrolytic enzyme (starting enzyme) and a component that stabilizes the hydrolytic enzyme and that comprises a reversible inhibitor of the hydrolytic enzyme; b) changing the amino acid sequence of the hydrolytic enzyme in at least one position, by substitution, deletion or insertion; c) determining the relative activity of the hydrolytic enzyme from step b) and the relative activity of the starting enzyme in a liquid preparation; d) selecting the hydrolytic enzyme that has a reduced relative activity by comparison with the relative activity of the starting enzyme.

7 Claims, No Drawings

(56) References Cited

OTHER PUBLICATIONS

Keller et al., "Probing the Specificity of the S1 Binding Site of Subtilisin Carlsberg with Boronic Acids", Biochemical and Biophysical Research Communications, vol. 176, No. 1, pp. 401-405, 1991.

Seufer-Wasserthal et al., "Probing the Specificity of the S1 Binding Site of Subtilisin Carlsberg with Boronic Acids", Bioorganic & Medicinal Chemistry, vol. 2, No. 1, pp. 35-48, 1994.

Altschul et al., "Gapped BLAST and PSI-BLAST: A New Generation of Protein Database Search Programs", Nucleic Acids Research, vol. 25, No. 17, pp. 3389-3402, 1997.

Notredame et al., "T-Coffee: A Novel Method for Fast and Accurate Multiple Sequence Alignment", Journal of Molecular Biology, vol. 302, pp. 205-217, 2000.

Chenna et al., "Multiple Sequence Alignment with the Clustal Series of Programs", Nucleic Acids Research, vol. 31, No. 13, pp. 3497-3500, 2003.

* cited by examiner

SEQUENCE LISTING

```
<160> NUMBER OF SEQ ID NOS: 3

<210> SEQ ID NO 1
<211> LENGTH: 275
<212> TYPE: PRT
<213> ORGANISM: Bacillus amyloliquefaciens

<400> SEQUENCE: 1

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30
```

```
Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
 1               5                  10                  15

Leu Pro Asn Asp Gly Asn His Trp Asn Arg Leu Arg Ser Asp Ala Ser
                 20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Ile Arg Thr Lys Tyr Gly
 65                  70                  75                  80

Thr Arg Asn Gln Leu Gln Ala Ala Val Asn Ala Leu Lys Ser Asn Gly
                 85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
```

```
            115                 120                 125
Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 3
<211> LENGTH: 269
<212> TYPE: PRT
<213> ORGANISM: Bacillus lentus

<400> SEQUENCE: 3
```

-continued

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50              55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

METHOD FOR ADAPTING A HYDROLYTIC ENZYME TO A COMPONENT THAT STABILIZES THE HYDROLYTIC ENZYME

FIELD OF THE INVENTION

The present invention generally relates to enzyme technology, and more particularly relates to a method, in which a hydrolytic enzyme, in particular a protease, is adapted to an enzyme stabilizer and consequently is optimized for it. The invention further relates to hydrolytic enzymes that can be obtained with such a method.

BACKGROUND OF THE INVENTION

Problems relating to the shelf stability of enzyme-containing preparations, for example of enzyme preparations or of washing or cleaning agents or disinfectants, are known from the prior art. This problem is especially acute with liquid enzyme preparations or liquid enzyme-containing surfactant preparations, for example liquid washing or cleaning agents. After only a short time they lose a significant degree of enzymatic, in particular hydrolytic, and especially proteolytic activity. The surfactant preparation, for example the washing or cleaning agent or disinfectant, then no longer exhibits optimum cleaning performance. One objective in the development of enzyme-containing surfactant preparations is therefore to stabilize the contained enzymes and to protect them from denaturing and/or cleavage and/or degradation, in particular during storage and/or during utilization of the preparation. Hydrolytic enzymes in particular, and especially proteases, but for example also amylases, are of interest in this regard. For this, chemical compounds that in particular reversibly inhibit proteases, can be added to the preparations and thereby act all in all as stabilizers for the proteases and other comprised enzymes. The inhibitors have to be reversible in this case, as the enzyme activity should only be temporarily prevented, in particular during storage, but no longer during the cleaning process.

Boric acid and boric acid derivatives, even at a comparatively low concentration, occupy a prominent position among the enzyme stabilizers that are effective in surfactant preparations. International patent application WO 96/21716 A1, for example, discloses that boric acid derivatives and boronic acid derivatives acting as protease inhibitors are suitable for stabilizing enzymes in liquid preparations, among them washing and cleaning agents. A selection of boronic acid derivatives as stabilizers is disclosed, for example, in the international patent application WO 96/41859 A1. Meta- and/or para-substituted phenylboronic acids are presented as enzyme stabilizers in WO 92/19707 A1 and EP 478050 A1. Complexes of boric acids and boric acid derivatives with aromatic compounds are disclosed in EP 511456 A1 as enzyme stabilizers in liquid detergent compositions.

Boric acids and boric acid derivatives have the disadvantage, however, that they form undesired secondary products with other ingredients of a surfactant preparation, in particular the ingredients of washing or cleaning agents or disinfectants, such that they are no longer available in the relevant agents for the desired cleaning purpose, or in fact remain behind, for example on the washed item, as a contaminant. In addition, boric acids and borates are increasingly considered to be disadvantageous in environmental terms.

Indeed, boric acid-free or boron-free compounds are known from the prior art to reversibly inhibit hydrolytic enzymes and thus stabilize them. However, they frequently have the disadvantage that they do not adequately stabilize the enzymes in a preparation of the enzyme, in particular not in liquid surfactant preparations such as for example in washing or cleaning agents or disinfectants. In order to bring about a satisfactory stabilization, such compounds would frequently have to be employed in such a great amount, thereby making their use impossible, as these amounts cannot be satisfactorily incorporated into the enzyme preparation and/or their incorporation becomes economically unviable.

The underlying object of the present invention is to adapt a hydrolytic enzyme to a component that stabilizes the hydrolytic enzyme, in particular a reversible inhibitor, and consequently to improve its stabilization by these components.

The component that stabilizes the enzyme should preferably contain as little as possible boric acid or boron-containing compounds or preferably, should be free of boric acid and/or boron.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A method for adapting a hydrolytic enzyme to a component that stabilizes the hydrolytic enzyme, comprising the process steps a) providing a hydrolytic enzyme (starting enzyme) and a component that stabilizes the hydrolytic enzyme, said component comprising a reversible inhibitor of the hydrolytic enzyme; b) modifying the amino acid sequence of the hydrolytic enzyme at at least one position by substitution, deletion or insertion; c) determining the relative activity of the hydrolytic enzyme from step b) and the relative activity of the starting enzyme in a liquid preparation; d) selecting that hydrolytic enzyme that exhibits a diminished relative activity in comparison to the relative activity of the starting enzyme.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Subject matter of the invention is a method for adapting a hydrolytic enzyme to a component that stabilizes the hydrolytic enzyme, comprising the process enzyme in a liquid preparation;

a) providing a hydrolytic enzyme (starting enzyme) and a component that stabilizes the hydrolytic enzyme, said component comprising a reversible inhibitor of the hydrolytic enzyme;

b) modifying the amino acid sequence of the hydrolytic enzyme on at least one position by substitution, deletion or insertion;

c) determining the relative activity of the hydrolytic enzyme from step b) and the relative activity of the starting enzyme in a liquid preparation;

d) selecting that hydrolytic enzyme that exhibits a diminished relative activity in comparison to the relative activity of the starting enzyme.

An inventive method can additionally comprise the following process step(s):

e) optional repetition of the process steps b) to d), until the hydrolytic enzyme has a diminished relative activity in comparison to the relative activity of the starting enzyme.

Contrary to the methodology established in the prior art: to discover for a given hydrolytic enzyme a component that stabilizes this enzyme, the opposite approach will be inventively taken, namely that of modifying the hydrolytic enzyme and thereby adapting it to the component that stabilizes the hydrolytic enzyme (enzyme stabilizer), in particular to the reversible inhibitor, such that an improved stabilization of the modified hydrolytic enzyme is achieved by the component that stabilizes the hydrolytic enzyme. The matching stabilizer for an enzyme will not be sought; rather the enzyme will be optimized for its stabilization by the given stabilizer. It was found that it is advantageous to adapt the hydrolytic enzyme to the component that stabilizes the hydrolytic enzyme, and not the other way round. In this manner for example, advantageous combinations of enzyme and stabilizing compound can be quickly identified. In a preferred development these kinds of combinations afford an improved enzyme inhibition and/or enzyme stabilization by the stabilizing compound, in particular in a liquid washing or cleaning agent or disinfectant. This opens up the possibility of using less boron-containing compounds as enzyme stabilizers in liquid preparations, in particular liquid surfactant preparations. In particular, in particularly preferred developments it is possible to partly or preferably entirely eliminate boric acid as an enzyme stabilizer in a liquid surfactant preparation, such that the preparation can be free of boric acid. In particularly advantageous developments, a surfactant preparation of this kind can ideally be free of boron.

In addition, inventively adapted combinations of enzyme stabilizer and hydrolytic enzyme preferably have the advantage that the enzyme stabilizer already exerts its stabilizing effect at low to very low concentrations. In addition, it can be selected, such that it preferably has a good solubility in water. Therefore, together with the enzyme stabilized by it, it can easily be incorporated into an aqueous liquid preparation, in particular a surfactant preparation and thus preferably into a liquid washing or cleaning agent or disinfectant. Advantageously, any precipitation during storage is moreover decreased or entirely avoided.

A hydrolytic enzyme is a hydrolase (EC 3.X.X.X) and thus an enzyme that hydrolytically cleaves esters, ethers, peptides, glycosides, acid anhydrides, or carbon-carbon bonds in a reversible reaction. The hydrolytic enzyme therefore catalyzes the hydrolytic cleavage of substances as defined by: A-B+$H_2O$↔AH+B—OH. Hydrolases form the third main class in the EC classification of enzymes. The EC (Enzyme Commission) numbers constitute a numerical classification system for enzymes. Each EC number is made up of four numbers separated by periods; the first digit identifies one of the six main enzyme classes, and hydrolases (EC 3.X.X.X) correspondingly represent the third main class. Its representatives are proteases, peptidases, nucleases, phosphatases, glycosidases, and esterases. The hydrolytic enzyme is particularly preferably a protease.

Process step a) provides a hydrolytic enzyme as well as a component that stabilizes the hydrolytic enzyme and which contains a reversible inhibitor of the hydrolytic enzyme. A reversible inhibitor of the hydrolytic enzyme is consequently any compound that is capable of a reversible non-covalent interaction with the hydrolytic enzyme and diminishes the catalytic activity of the hydrolytic enzyme as a result of its interaction with the enzyme. The hydrolytic enzyme is therefore stabilized due to its inhibition by the reversible inhibitor, preferably in an aqueous environment. In the context of the present invention, water itself is consequently not a component that stabilizes the hydrolytic enzyme. The molecular mass of the reversible inhibitor of the hydrolytic enzyme is preferably at least 20 g/mol and increasingly preferably at least 25, 30, 35, 40, 45, 50, 55, 60, 65, 70 g/mol. In this regard, it further preferably concerns an organic chemical compound.

The reversible inhibitor in regard to the hydrolytic enzyme in process step a) preferably has an inhibition constant ($K_i$) of 0.01 to 500 mM, preferably 0.01 to 100 mM, particularly preferably 0.01 to 1 mM or 10 to 100 mM.

The inhibition constant $K_i$ is a characteristic and decisive factor for characterizing a reversible inhibitor of enzymatic activity $K_i$ describes the equilibrium between enzyme, inhibitor and enzyme-inhibitor complex for a reversible binding. Here, the enzyme-inhibitor complex is not catalytically active and inhibits the reaction by reducing the concentration of free enzyme that is still available for binding the substrate. Accordingly, $K_i$ is defined as:

$$K_i = [I] \times [E]/[EI]$$

where [E], [I] and [EI] mean the respective molar equilibrium concentrations of enzyme (E), inhibitor (I) and the enzyme-inhibitor complex (EI). In accordance with this definition, a substance with a small $K_i$ is a good inhibitor under the respective test conditions.

$K_i$ is determined based on the activity test of the protease in the presence of the corresponding inhibitor. The enzymatic parameter $K_m$, and $k_{cat}$ in the presence of various concentrations of the inhibitor are determined using Michaelis-Menten kinetics, which are established in the prior art and known to the person skilled in the art (Leonor Michaelis, Maud Menten (1913), Die Kinetik der Invertinwirkung, Biochem. Z. 49.333-369). For Michaelis-Menten kinetics one can simply apply:

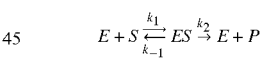

$$E + S \underset{k_{-1}}{\overset{k_1}{\rightleftarrows}} ES \overset{k_2}{\rightarrow} E + P$$

In which:
E: Enzyme
S: Substrate
ES: Enzyme-substrate complex
P: Product
$k_{-1}$, $k_1$, $k_2$: rate constants
where $k_2$ is a measure of the maximum reaction rate for substrate saturation (Vmax), also called turnover frequency, molecular activity, turnover number or kcat (kcat=Vmax/[Eo], where [Eo] is the starting concentration of the enzyme). The Michaelis constant (i.e. the substrate concentration at which the reaction rate is at half maximum, thus when v=Vmax/2) results in
$K_m = k_{-1}/k_1$ (Michaelis-Menten case, given when $k_2 \ll k_{-1}$) or more generally to
$K_m = k_{-1} + k_2/k_1$ (Briggs-Haldane situation, given for the case when $k_2$ against $k_{-1}$ cannot be neglected).

The saturation function of a "Michaelis-Menten enzyme" is obtained by using the parameters Km and Vmax as follows:

$$v = \frac{v'_{max}[S]}{K_m + [S]}$$

in which: v: rate of formation of P (v="rate") [mol l$^{-1}$ s$^{-1}$]
vmax: maximum rate [mol l$^{-1}$ s$^{-1}$]
Km: Michaelis-Menten constant [mol l$^{-1}$]
[S]: Substrate concentration [mol l$^{-1}$]

The inhibition constant $K_i$ is obtained by determining the initial catalyst rate ($v_{Anf}$)—for proteases the initial rate of hydrolysis—for various substrate concentrations [S] and inserting the experimental data into the following equation 1.

$$v_{Anf} = k_{cat} \times [S] \times E_0 / (K_m \times (1+[I]/K_i) + S) \quad \text{Equation 1}$$

where [I] again stands for the inhibitor concentration.

Alternatively, $K_i$ can be determined by using the Cheng-Prusoff equation (equation 2, Cheng Y., Prusoff W. H. (1973) *Biochem. Pharmacol.* 22, 3099-3108) through the IC$_{50}$-value. The IC$_{50}$-value is determined by determining the catalytic activity on a substrate in the presence of various concentrations of the inhibitor and inserting the experimental data into a sigmoid dose-response equation with variable slope (pseudo-Hill slopes). This is the inhibitor concentration that would be needed to achieve a 50% inhibition. $K_i$ is thus obtained from the following equation 2:

$$K_i = IC_{50}/(1+[S]/K_d) \quad \text{Equation 2}$$

wherein [S] means the substrate concentration in the test and $K_d$ means the dissociation constant for the substrate which for the IC$_{50}$-concentration of the inhibitor can be set as identical with $K_m$ for the substrate.

The thus determinable $K_i$ values characterize the reversible inhibitor with respect to the utilized enzyme, thus for example the reversible protease inhibitor with respect to the utilized protease.

The component that stabilizes the hydrolytic enzyme can consist entirely of the reversible inhibitor, such that the component that stabilizes the hydrolytic enzyme (enzyme stabilizer) is the reversible inhibitor. This development is particularly preferred.

Alternatively, the component that stabilizes the hydrolytic enzyme can include additional compounds, such that the respective reversible inhibitor is a part of the component that stabilizes the hydrolytic enzyme. In particular, the component that stabilizes the hydrolytic enzyme can include combinations of different reversible inhibitors.

The component that stabilizes the hydrolytic enzyme (in addition to the inhibiting effect of the reversible inhibitor) preferably also already brings about a storage stability of the hydrolytic enzyme in an aqueous environment. The storage stability is then preferably further improved by an inventive method, in that the hydrolytic enzyme is adapted to the component that stabilizes the hydrolytic enzyme, in particular to the reversible inhibitor.

A storage stability exists when the presence of the component that stabilizes the hydrolytic enzyme causes an aqueous liquid preparation that contains hydrolytic enzyme and the component that stabilizes the hydrolytic enzyme (stabilized preparation) to exhibit a higher enzymatic residual activity of the hydrolytic enzyme after storage in comparison to a control preparation that differs from the stabilized preparation only in the absence of the component that stabilizes the hydrolytic enzyme (control). In this regard, the component that stabilizes the hydrolytic enzyme is comprised in the stabilized preparation in an amount of 0.002 to 0.35 wt %. After storage this preparation therefore exhibits a higher residual activity of the hydrolytic enzyme in comparison to the control, wherein the stabilized preparation and the control exhibit the same enzymatic initial activity at the start of the storage, both preparations being treated in the same manner, in particular concerning the storage conditions and the determination of the enzyme activity. Storage is preferably carried out for at least 48 hours at a temperature of 20° C., 25° C. or 30° C. The storage is increasingly preferably carried out for at least 72 hours, 5 days, 1 week, 2 weeks, 3 weeks, 4 weeks, 5 weeks, 6 weeks, 7 weeks or 8 weeks at a temperature of 20° C., 25° C. or 30° C. for the entire storage period.

The presence of a storage stability is particularly preferably determined i. for a protease-containing liquid preparation by using this protease-containing liquid preparation that is stored for at least 48 hours at a temperature of 30° C. and its proteolytic residual activity is determined by the release of the chromophore para-nitroaniline (p-NA) from the substrate suc-AAPF-pNA as presented further below; and/or ii. for an amylase-containing liquid preparation by using this amylase-containing, preferably protease-free, liquid preparation that is stored for at least 48 hours at a temperature of 30° C. and whose amylolytic residual activity is determined as presented further below.

For clarification purposes it should be noted here that in process step a) according to the invention, at least one reversible inhibitor of the hydrolytic enzyme is present, whose inhibiting effect preferably—but not necessarily—already brings about a storage stability of the hydrolytic enzyme, wherein the storage stability is preferably determined as described above. The presence of a storage stability is, however, not essential for the mere detection of an inhibiting effect of a compound on a hydrolytic enzyme—in this regard the determination of the activity of the hydrolytic enzyme in the absence and presence of the compound is decisive. Therefore, one must differentiate between the inhibiting effect and storage stability. A reversible inhibitor exhibits an inhibiting effect—this preferably determines, but not necessarily, storage stability.

In order to adapt the hydrolytic enzyme to the component that stabilizes the hydrolytic enzyme, in particular to the reversible inhibitor, in process step b) the amino acid sequence of the hydrolytic enzyme is modified at at least one position by substitution, deletion or insertion. Moreover, a plurality of substitutions, deletions or insertions can also be made. According to the invention, any combinations of one or more substitutions, deletions or insertions can also be made. The introduction of such mutations into an amino acid sequence is commonly used by the person skilled in the art of enzyme technology and is preferably carried out by modifying the nucleic acid sequence that codes for the hydrolytic enzyme. The modified enzyme itself is then obtained by expression of this nucleic acid sequence in a suitable host and optionally subsequently purified. In the case of an insertion, the amino acid to be inserted is inserted after the respective amino acid (i.e. C-terminal).

In process step c) the relative activity of the hydrolytic enzyme that was modified in process step b) is determined, together with that of the starting enzyme. For the determination of the relative activity, the activity determination for an enzyme has to be carried out in a liquid preparation both in the absence as well as the presence of the component that stabilizes the hydrolytic enzyme, in particular in an aqueous preparation.

The liquid preparation is preferably constituted as follows (all data in wt %): 0.3-0.5% xanthane, 0.2-0.4% defoamer, 6-7% glycerin, 0.3-0.5% ethanol, 4-7% FAEOS (fatty alcohol ether sulfate), 24-28% non-ionic surfactants, 1-2% sodium citrate (dihydrate), 2-4% soda, 14-16% cocoanut fatty acids, 0.5% HEDP, (1-hydroxyethane-(1,1-diphosphonic acid)), 0-0.4% PVP (polyvinyl pyrrolidone) 0-0.5% optical brightener, 0-0.001% % colorant, remainder being demineralized water. A preparation of this type or a 50% conc. aqueous solution of it is particularly preferably used for the determination of the relative activity.

In this regard, the enzyme activity is determined using standard methods matched to the particular enzyme type. Methods for determining the enzyme activities are well known to the person skilled in the field of enzyme technology and are routinely used by him/her. Methods for determining protease activity are disclosed, for example, in *Tenside*, Vol. 7 (1970), pp. 125-132. The proteolytic activity is preferably determined by way of the release of the para-nitroaniline (pNA) chromophore from the suc-L-Ala-L-Ala-L-Pro-L-Phe-p-nitroanilide substrate (suc-AAPF-pNA). The protease cleaves the substrate and releases pNA. The released pNA causes the extinction at 410 nm to increase; the change in extinction as a function of time is a measure of the enzymatic activity (see Del Mar et al., 1979). The measurement is carried out at a temperature of 25° C., at pH 8.6 and a wavelength of 410 nm. The measurement period is 5-10 minutes with a measurement interval of 20 s to 60 s.

Amylolytic activity can be determined as follows: Under defined reaction conditions (tris-maleate buffer pH 6.5, 50° C., 15 min), the samples to be investigated are incubated with 0.67% starch (FLUKA no. 85642; from potatoes, soluble, pretreated per Zulkowsky (treated with glycerin at 190° C.)) as the substrate. By adding dinitrosalicylic acid and with heating to 100° C. it is reduced by glucose and other reducing sugars to afford an orange-red dye that at the end of the reaction is measured photometrically at a wavelength of 540 nm. The quantity of released sugar corresponding to the color is an indication of the enzyme activity.

The relative activity to be determined in process step c) of the hydrolytic enzyme modified in process step b) is given by [measured activity of the hydrolytic enzyme modified in process step b) in the presence of the component that stabilizes the hydrolytic enzyme] divided by [measured activity of the hydrolytic enzyme modified in process step b) in the absence of the component that stabilizes the hydrolytic enzyme] multiplied by 100.

The relative activity of the starting enzyme to be determined in process step c) is given by [measured activity of the starting enzyme in the presence of the component that stabilizes the hydrolytic enzyme] divided by [measured activity of the starting enzyme in the absence of the component that stabilizes the hydrolytic enzyme] multiplied by 100.

The determination of the activities and consequently also the determination of the relative activities of the hydrolytic enzyme (originating from process step b; test preparations, each with and without stabilizing component) and starting enzyme (control preparations, each with and without stabilizing component) is carried out under identical conditions, such that the resulting relative activities can be compared. Test preparations and control preparations consequently differ only in the enzyme used, each in the absence and presence of the stabilizing component.

It is also advantageous when determining the activities if the concentration of the component that stabilizes the hydrolytic enzyme is selected in such a way that for the starting enzyme in the control preparation with the stabilizing component there is between 90%-60% of the activity of the control preparation without stabilizing component.

In process step d) the relative activity of the hydrolytic enzyme that was modified in process step b) and determined in process step c) is compared with the relative activity of the starting enzyme, and then that hydrolytic enzyme is selected which has a reduced activity in comparison to the relative activity of the starting enzyme. Preferably, that hydrolytic enzyme is selected, which exhibits a relative activity reduced by at least 1%, 2%, 3%, 4%, 5%, 6%, 7%, 8%, 9%, 10%, 12.5%, 15%, 17.5%, 20%, 22.5%, 25%, 27.5%, 30%, 32.5%, 35%, 37.5% and 40% in comparison to the relative activity of the starting enzyme.

Optionally the process steps b) to d) can be repeated, until the hydrolytic enzyme has a diminished relative activity in comparison to the relative activity of the starting enzyme. The thus obtained hydrolytic enzyme then preferably exhibits a relative activity reduced by at least 1%, 2%, 3%, 4%, 5%, 6%, 7%, 8%, 9%, 10%, 12.5%, 15%, 17.5%, 20%, 22.5%, 25%, 27.5%, 30%, 32.5%, 35%, 37.5% and 40% in comparison to the relative activity of the starting enzyme.

A hydrolytic enzyme obtained in this way, in particular a protease, is inhibited more by the reversible inhibitor of the component that stabilizes the hydrolytic enzyme. Subsequently, this improved inhibiting effect also brings about an improved stabilization of the hydrolytic enzyme. An improved inhibition of the hydrolytic enzyme is consequently associated with its improved stabilization. The improved stabilization can be determined in a storage test as described above.

In another embodiment of the invention, a method according to the invention is wherein the hydrolytic enzyme is a protease, amylase, cellulase, glycosidase, hemicellulase, mannanase, xylanase, xyloglucanase, xanthanase, a pectin-cleaving enzyme, β-glucosidase, carrageenase or a lipase or a mixture that comprises at least two of these enzymes.

Examples of proteases are the subtilisins BPN' from *Bacillus amyloliquefaceans* and Carlsberg from *Bacillus licheniformis*, the protease PB92, the subtilisins 147 and 309, the protease from *Bacillus lentus*, subtilisin DY, and the enzymes (to be classified, however, as subtilases and no longer as subtilisins in the strict sense) thermitase, proteinase K, and the proteases TW3 and TW7. Subtilisin Carlsberg is obtainable in a further developed form under the trade name Alcalase® from Novozymes A/S, Bagsvaerd, Denmark. The subtilisins 147 and 309 are commercialized under the trade names Esperase® and Savinase® by the Novozymes Company. The protease variants sold under the name BLAP® are derived from the protease from *Bacillus lentus* DSM 5483. Other usable proteases are, for example, the enzymes obtainable under the trade names Durazym®, Relase®, Everlase®, Nafizym®, Natalase®, Kannase®, and Ovozyme® from Novozymes, under the trade names Purafect®, Purafect® OxP, Purafect® Prime, Excellase®, and Properase® from Danisco/Genencor, under the trade name Protosol® from Advanced Biochemicals Ltd., Thane, India, under the trade name Wuxi® from Wuxi Snyder Bioproducts Ltd., China, under the trade names Proleather® and Protease P® from Amano Pharmaceuticals Ltd., Nagoya, Japan, and under the designation Proteinase K-16 from Kao Corp., Tokyo, Japan. The proteases from *Bacillus gibsonii* and *Bacillus pumilus*, which are disclosed in international patent applications WO 08/086,916 and WO 07/131,656, are also used with particular preference. Further advantageously usable proteases are disclosed in patent applications WO 91/02792, WO 08/007,319, WO 93/18140, WO 01/44452, GB 1243784, WO 96/34946, WO 02/029024, and WO 03/057246. Further usable proteases are those that are naturally present in the microorganisms *Stenotrophomonas maltophilia*, in particular *Stenotrophomonas maltophilia* K279a, *Bacillus intermedius*, and *Bacillus sphaericus*.

Examples of amylases are the α-amylases from *Bacillus licheniformis*, from *Bacillus amyloliquefaciens*, or from *Bacillus stearothermophilus*, and in particular the further developments thereof improved for use in washing or cleaning agents. The enzyme from *Bacillus licheniformis* is available from the Novozymes Company under the name Termamyl® and from the Danisco/Genencor Company under the name Purastar® ST.

Further development products of this α-amylase are available from Novozymes under the trade names Duramyl® and Termamyl® ultra, from Danisco/Genencor under the name Purastar® OxAm, and from Daiwa Seiko Inc., Tokyo, Japan, as Keistase®. The α-amylase from *Bacillus amyloliquefaciens* is marketed by Novozymes under the name BAN®, and derived variants of the α-amylase from *Bacillus stearothermophilus* are marketed, again by Novozymes, under the names BSG® and Novamyl®. Additionally to be highlighted for this purpose are the α-amylase from *Bacillus* sp. A 7-7 (DSM 12368) and the cyclodextrin-glucanotransferase (CGTase) from *Bacillus agaradherens* (DSM 9948). Also usable are the amylolytic enzymes that are disclosed in international patent applications WO 03/002711, WO 03/054177, and WO 07/079,938. Fusion products of all the cited molecules can also be employed. Moreover, further developments of α-amylase from *Aspergillus niger* and *A. oryzae* available from the Novozymes Company under the trade name Fungamyl® are suitable. Additional commercial products that can be advantageously used are for example the Amylase-LT® and Stainzyme® or Stainzyme Ultra® or Stainzyme Plus®, the last also from the Novozymes Company. Variants of these enzymes obtained by point mutations can also be inventively employed.

Examples of cellulases (endoglucanases, EG) are the fungus-based cellulase preparation rich in endoglucanase (EG), or its further developments, offered by the Novozymes company under the trade name Celluzyme®. The products Endolase® and Carezyme®, likewise obtainable from the Novozymes Company, are based on the 50 kD EG and 43 kD EG, respectively, from *Humicola insolens* DSM 1800. Further usable commercial products of this company are Cellusoft®, Renozyme®, and Celluclean®. Cellulases, for example, which are available under the trade names Ecostone® and Biotouch® from AB Enzymes, Finland can also be used and which are at least partially based on the 20 kD-EG from Melanocarpus. Additional cellulases from the AB Enzymes Company are Econase® and Ecopulp®. Further suitable cellulases are from *Bacillus* sp. CBS 670.93 and CBS 669.93, the CBS 670.93 from *Bacillus* sp. being available under the trade name Puradax® from the Danisco/Genencor Company. Other useable commercial products of the Danisco/Genencor Company are "Genencor detergent cellulase L" and IndiAge®Neutra.

Further preferred hydrolytic enzymes are those grouped under the term glycosidases (EC 3.2.1.X). These include in particular arabinases, fucosidases, galactosidases, galactanases, arabico-galactan-galactosidases, mannanases (also called mannosidases or mannases), glucuronosidases, agarase, carrageenases, pullulanases, β-glucosidases, xyloglucanases (xylanases), xanthanases, and pectin-degrading enzymes (pectinases). Preferred glycosidases are also grouped under the term hemicellulases. Included among the hemicellulases are, in particular, mannanases, xyloglucanases (xylanases), β-glucosidases, and carrageenases, as well as further pectin-cleaving enzymes, pullulanases, and β-glucanases.

In the context of the invention, pectin-cleaving enzymes (pectinases) are enzymes that cleave pectin and/or other galacturonanes. Pectinases concern polysaccharides, whose major constituent is α-D-Galacturonic acid as the monomer, preferably to at least 50 wt % and particularly preferably to at least 65 wt %. These galacturonic acid monomers are linked together though α-1,4-, sometimes also with a minor fraction through β-1,4-glycosidic bonds, and form the backbone of the pectin molecule that is periodically interrupted by 1,2-bonds with α-L-rhamnose. Consequently, pectin is a rhamno-galacturonic acid. Consequently, a pectin-cleaving enzyme is in particular an enzyme that catalyzes the hydrolysis of 1,4-α-D-galactosiduronic bonds.

Within the EC Classification of enzymes, in the numerical classification system for enzymes, the pectin-cleaving enzymes particularly belong to the enzyme classes (Enzyme Commission number) EC 3.1.1.1 1, EC 3.2.1.15, EC 3.2.1.67 and EC 3.2.1.82, and consequently fall into the third of the six major classes of enzymes, the hydrolases (E.C.3. -.-.-), sub-classification glycosylases (E.C. 3.2.-.-) and again sub-classification glycosidases (E.C. 3.2.1.-), i.e. enzymes that hydrolyse O- and/or S-glycosyl compounds. Consequently, pectin-cleaving enzymes are effective particularly against residues on dishes which comprise pectic acid and/or other galacturonanes, and catalyze their hydrolysis.

In the context of the present invention, the pectin-cleaving enzymes likewise include enzymes with the names pectinase, pectolyase, pectinesterase, pectindemethoxylase, pectinmethoxylase, pectinmethylesterase, pectase, pectinmethylesterase, pectinoesterase, pectinpectylhydrolase, pectindepolymerase, endopolygalacturonase, pectolase, pectinhydrolase, pectin-polygalacturonase, endopolygalacturonase, poly-α-1,4-galacturonide glycanohydrolase, endogalacturonase, endo-D-galacturonase, galacturan 1,4-α-galacturonidase, exopolygalacturonase, poly(galacturonate) hydrolase, exo-D-galacturonase, exo-D-galacturonanase, exopoly-D-galacturonase, exo-poly-α-galacturonosidase, exo-polygalacturonosidase or exopolygalacturanosidase.

Exemplary suitable enzymes are available for example under the names Gamanase®, Pektinex ARC), X-Pect® or Pectaway® from Novozymes, under the name Rohapect UF®, Rohapect TPL®, Rohapect PTE100®, Rohapect MPE®, Rohapect MA plus HC, Rohapect DA12L®, Rohapect 10L®, Rohapect B1 L® from AB Enzymes and under the name Pyrolase® from Diversa Corp., San Diego, Calif., USA.

Another example is the β-glucanase obtained from *Bacillus subtilis* which is available under the trade name Cereflo® from the Novozymes company. Glycosidases or hemicellulases that are inventively particularly preferred are mannanases, which are marketed e.g. under the trade names Mannaway® by Novozymes or Purabrite® by Danisco/Genencor.

Examples of lipases or cutinases are the lipases obtainable originally from *Humicola lanuginosa* (*Thermomyces lanuginosus*) or lipases further developed therefrom, in particular those having the D96L amino acid exchange. They are commercialized, for example by the Novozymes Company under the trade names Lipolase®, Lipolase® Ultra, LipoPrime®, Lipozyme® and Lipex®. A further advantageously usable lipase is obtainable from the Novozymes company under the trade name Lipoclean®. Moreover, suitable cutinases, for example, are those that were originally isolated from *Fusarium solani pisi* and *Humicola insolens*. Likewise useable lipases are available from the Amano Company under the designations Lipase CE®, Lipase P®, Lipase B®, and Lipase CES®, Lipase AKG®, *Bacillis* sp. Lipase®, Lipase AP®, Lipase M-AP® and Lipase AML®. Suitable lipases or cutinases whose starting enzymes were originally isolated from *Pseudomonas mendocina* and *Fusarium solanii* are for example available from the Danisco/Genencor Company. Further important commercial products that may be mentioned are the commercial preparations M1 Lipase® and Lipomax® originally from Gist-Brocades Company (now Danisco/Genencor), and the commercial enzymes from the Meito Sangyo KK Company, Japan under the names Lipase MY-30®, Lipase OF® and Lipase PL® as well as the product Lumafast® from the Danisco/Genencor Company.

In the context of the present invention, the useable enzymes either stem originally from microorganisms, such as the genera *Bacillus, Streptomyces, Humicola* or *Pseudomonas*, and/or are produced according to known biotechnological processes using suitable microorganisms, such as by transgenic expression hosts, for example the genus *Bacillus* or by filamentary fungi.

The hydrolytic enzyme is particularly preferably a protease and/or an amylase. The hydrolytic enzyme is quite particularly preferably a protease. Among the proteases a serine protease is preferred, a subtilase is also preferred and a subtilisin is quite particularly preferred. It has been shown that proteases, in particular those proteases by a method according to the invention, can be adapted particularly well to a component that stabilizes the hydrolytic enzyme, in particular in a liquid surfactant preparation. The same applies for amylases, which can be adapted particularly well by a method according to the invention to a component that stabilizes the hydrolytic enzyme, in particular in a liquid surfactant preparation. The storage stability of the enzymes and particularly that of proteases and/or amylases is a general problem, particularly for washing or cleaning agents or disinfectants.

With regard to proteases as the preferred hydrolytic enzymes, the stabilizing component consequently contains a reversible protease inhibitor. Proteases are frequently responsible for the lack of enzyme stability in liquid preparations, in that they hydrolyze the comprised enzymes. Consequently, a reversible protease inhibitor can improve the enzyme stability in liquid preparations, in that the proteolytic activity is inhibited in the preparation and the inhibition of the proteolytic activity is removed again only when needed, for example by diluting the preparation, in particular with water. The protease inhibitors must be reversible as the protease activity should only be temporarily prevented, in particular during storage, but no longer during the proposed usage of the liquid preparation, for example during the cleaning process. A greater inhibition of the proteases in the liquid preparation leads to a greater stabilization of the proteases and of other enzymes. Consequently, protease inhibitors according to the invention reversibly inhibit the protease activity and in this way stabilize the proteases and other enzymes, in particular due to the reduction in proteolytic activity of the proteases by the inhibitor. A greater inhibition of the proteases leads to a higher stability of the proteases and of other enzymes, for example due to the increased protection against proteolytic degradation. In another preferred embodiment of the invention, a method according to the invention is wherein the hydrolytic enzyme is a protease and the component that stabilizes the hydrolytic enzyme contains a reversible protease inhibitor.

In another preferred embodiment of the invention, a method according to the invention is wherein the protease is modified at a position that corresponds to the position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274 or 275 in SEQ ID NO. 1, assigned in an alignment with SEQ ID NO. 1, or that the amylase is modified at a position that corresponds to the position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484 or 485 in SEQ ID NO. 2, assigned in an alignment with SEQ ID NO. 2.

The alignment of the amino acid positions as well as the identity of nucleic acid or amino acid sequences are determined by a sequence comparison. This comparison is made by aligning similar sequences in the nucleotide sequences or amino acid sequences with one another. This sequence comparison is preferably carried out based on the BLAST algorithm that is established in the prior art and usually used (see for example Altschul, S. F., Gish, W., Miller, W., Myers, E. W. & Lipman, D J. (1990) "Basic local alignment search tool." *J. Mol. Biol.* 215: 403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; *Nucleic Acids Res.*, 25, pp. 3389-3402) and does so principally by aligning similar sequences of nucleotides or amino acids in the nucleic acid sequences or amino acid sequences with one another. A tabular assignment of the positions is called the alignment. Another algorithm that is available from the prior art is the FASTA algorithm. Sequence alignments, particularly multiple sequence alignments, are usually created with computer programs. The Clustal series for example are frequently used (see for example Chenna et al. (2003): Multiple sequence alignment with the Clustal series of programs, *Nucleic Acid Research* 31, 3497-3500), T-Coffee (see, for example Notredame et al. (2000): T-Coffee: A novel method for multiple sequence alignments. *J. Mol. Biol.* 302, 205-217) or programs that are based on these programs or algorithms. In the context of the present invention, sequence comparisons and alignments were preferably created with the software packet Vector NTI® Advance 10.3.0 (Invitrogen Corporation, 1600 Faraday Avenue, Carlsbad, Calif., USA) with the standard default parameters.

A comparison of this type allows on the one hand a statement to be made of the similarity of the compared sequences to one another. It is usually expressed in percent identity, i.e. in the fraction of the identical nucleotides or amino acid residues to the same positions or in an alignment to one another in corresponding positions. The wider term "homology" for amino acid sequences takes into consideration conserved amino acid exchanges, i.e. amino acids with similar properties, as they exercise mostly similar activities or functions within the protein. Consequently, the similarity of the compared sequences can also be expressed as percent homology or percent similarity. When not otherwise stated, identity or homology data in the present application refer to the total length of the relevant listed nucleic acid or amino acid sequence.

On the other hand a sequence comparison (alignment) enables the exact determination of the position in an amino acid sequence, which is aligned in a defined position in another amino acid sequence. Consequently, with the help of an alignment, it can be exactly determined which amino acid in which position in the protease to be inventively modified corresponds to one of the above-mentioned positions in the cited reference sequence. SEQ ID NO. 1 is the amino acid sequence of the protease BPN', SEQ ID NO. 2 is the amino acid sequence of the amylase, which is disclosed in SEQ ID NO. 4 of WO 2000/60060.

In another preferred embodiment of the invention, a method according to the invention is wherein the component that stabilizes the hydrolytic enzyme is comprised in an amount of 0.000001 to 10 wt %, 0.0001 to 5 wt %, 0.001 to 1 wt % and particularly preferably 0.002 to 0.35 wt % in the liquid preparation and/or the hydrolytic enzyme is comprised in an amount of $1\times10^{-8}$ to 5 wt % 0.00001-2 wt %, 0.001-1 wt %, 0.007 to 0.8 wt %, 0.025 to 0.5 wt % and particularly preferably 0.04 to 0.38 wt %, relative to the total protein content of the hydrolytic enzyme. The protein concentration can be determined using known methods, for example the BCA Process (bicinchoninic acid; 2,2'-biquinolyl-4,4'-dicarboxylic acid) or the biuret process (A. G. Gornall, C. S. Bardawill and M. M. David, *J. Biol. Chem.*, 177 (1948), pp. 751-766).

In another preferred embodiment of the invention, a method according to the invention is wherein the liquid preparation in process step c) is a surfactant preparation.

In the context of the present invention, a "surfactant preparation" is understood to mean any type of composition that comprises at least one surfactant. Such a composition preferably comprises a surfactant as described further below.

All liquid or free-flowing dosage forms can be used as the liquid surfactant preparation. In the context of the present application, "free-flowing" is understood to mean preparations that are pourable and can have viscosities up to several 10 000 mPas. The viscosity can be measured using standard methods (for example using a Brookfield-Viscosimeter LVT-II at 20 rpm and 20° C., spindle 3) and is preferably in the range of 5 to 10 000 mPas. Preferred agents have viscosities from 10 to 8000 mPas, particularly preferably from 120 to 3000 mPas. In the context of the present invention, a liquid surfactant preparation can therefore also be in gel form or in paste form, it can be a homogenous solution or suspension, it can be sprayable for example or be packaged in other usual dosage forms.

A liquid surfactant preparation according to the invention can be used as such or after dilution with water, especially for cleaning fabrics and/or hard surfaces. Such a dilution can be produced easily, in that a measured amount of the surfactant preparation is diluted in an additional amount of water in defined weight ratios of surfactant preparation:water, and optionally with shaking, in order to ensure a uniform distribution of the surfactant preparation in the water. Possible weight or volume ratios for the dilutions are from 1:0 surfactant preparation:water to 1:10000 or 1:20000 surfactant preparation:water, preferably from 1:10 to 1:2000 surfactant preparation:water.

In the context of the present invention, a surfactant preparation can therefore also be the washing or cleaning liquor itself. "Washing or cleaning liquor" is understood to mean that solution comprising the washing or cleaning agent which acts on textiles or fabrics (washing liquor) or on hard surfaces (cleaning liquor), and thereby comes into contact with the stains that are present on the textiles and/or fabrics or hard surfaces.

The washing or cleaning liquor usually comes into being when the washing or cleaning process begins and the washing or cleaning agent is dissolved or diluted with water, for example in a washing machine or in another suitable container.

In a preferred embodiment, the surfactant preparation is a washing agent, cleaning agent or disinfectant. Washing agents include all conceivable types of washing agents, especially washing agents for fabrics, carpets or natural fibers. They can be provided for manual and/or automatic use. The washing agents further include washing auxiliaries that in the course of a manual or automatic fabric wash are metered into the actual washing agent in order to achieve another effect. The cleaning agents include all agents, likewise in any cited dosage forms, for cleaning and/or disinfecting hard surfaces, manual and automatic dishwasher detergents, carpet cleaners, scouring agents, glass cleaners, WC-fragrant rinses, etc. Fabric pre- and after-conditioners are on the one hand those materials that are brought into contact with the washing prior to the actual wash, for example in order to partially dissolve intractable soils, and on the other hand those materials that in a step that follows on from the actual fabric wash, to confer additional desirable properties to the washing, such as a pleasant touch, absence of creasing or a low residual static charge. The last mentioned agents include inter alia the fabric softeners. Disinfectants are for example hand disinfectants, surface disinfectants and instrument disinfectants which can also be in any cited dosage form. A disinfectant preferably reduces germs by a factor of at least $10^4$, i.e. not more than a single survivor from an original 10 000 germs capable of reproduction (colony forming units—cfu), wherein viruses in this regard are not classified as germs as they do not possess cytoplasma and do not have their own metabolism. Preferred disinfectants reduce germs by a factor of at least $10^5$.

Anionic, non-ionic, zwitterionic and/or amphoteric surfactants can be added as the surfactant(s). Mixtures of anionic and non-ionic surfactants are preferred from the industrial application viewpoint. The total surfactant content of the liquid surfactant preparation is preferably below 60 wt % and particularly preferably below 45 wt %, based on the total liquid surfactant preparation.

Suitable non-ionic surfactants include alkoxylated fatty alcohols, alkoxylated fatty acid alkyl esters, fatty acid amides, alkoxylated fatty acid amides, polyhydroxyfatty acid amides, alkylphenol polyglycol ethers, amine oxides, alkyl polyglucosides and mixtures thereof.

Preferred non-ionic surfactants are alkoxylated, advantageously ethoxylated, particularly primary alcohols preferably containing 8 to 18 carbon atoms and, on average, 1 to 12 moles of ethylene oxide (EO) per mole of alcohol, in which the alcohol group may be linear or, preferably, methyl-branched in the 2-position or may contain e.g. linear and methyl-branched groups in the form of the mixtures typically present in Oxo alcohol residues. In particular, however, alcohol ethoxylates with linear alcohol groups of natural origin with 12 to 18 carbon atoms, for example from coco-, palm-, tallow- or oleyl alcohol, and an average of 2 to 8 EO per mole alcohol are preferred. Exemplary preferred ethoxylated alcohols include $C_{12-14}$ alcohols with 3 EO, 4 EO or 7 EO, $C_{9-11}$ alcohols with 7 EO, $C_{13-15}$ alcohols with 3 EO, 5 EO, 7 EO or 8 EO, $C_{12-18}$ alcohols with 3 EO, 5 EO or 7 EO and mixtures thereof, such as mixtures of $C_{12-14}$ alcohol with 3 EO and $C_{12-18}$ alcohol with 7 EO. The cited degrees of ethoxylation constitute statistically average values that can be a whole or a fractional number for a specific product. Preferred alcohol ethoxylates have a narrowed homolog distribution (narrow range ethoxylates, NRE). In addition to these non-ionic surfactants, fatty alcohols with more than 12 EO can also be used. Examples of these are tallow fatty alcohol with 14 EO, 25 EO, 30 EO or 40 EO. Also, non-ionic surfactants that comprise the EO and PO groups together in the molecule are employable according to the invention. Further suitable is also a mixture of a (highly) branched ethoxylated fatty alcohol and a linear ethoxylated fatty alcohol, such as for example a mixture of a $C_{16-18}$ fatty alcohol with 7 EO and 2-propylheptanol with 7 EO. The surfactant preparation particularly preferably comprises a $C_{12-18}$ fatty alcohol with 7 EO or a $C_{13-15}$ Oxo alcohol with 7 EO as the non-ionic surfactant.

The content of non-ionic surfactants is preferably 3 to 40 wt %, advantageously 5 to 30 wt % and particularly 7 to 20 wt %, in each case based on the total surfactant preparation.

The surfactant preparation can also comprise anionic surfactants in addition to the non-ionic surfactants. Sulfonates, sulfates, soaps, alkyl phosphates, anionic silicosurfactants and mixtures thereof are preferably employed as the anionic surfactant.

Suitable surfactants of the sulfonate type are, advantageously $C_{9-13}$ alkylbenzene sulfonates, olefin sulfonates, i.e. mixtures of alkene- and hydroxyalkane sulfonates and disulfonates, as are obtained, for example, from $C_{12-18}$ monoolefins having a terminal or internal double bond, by sulfonation with gaseous sulfur trioxide and subsequent alkaline or acidic hydrolysis of the sulfonation products. The $C_{12-18}$ alkane sulfonates and the esters of α-sulfofatty acids (ester sulfonates), e.g. the α-sulfonated methyl esters of hydrogenated coco-, palm nut- or tallow acids are also suitable.

Preferred alk(en)yl sulfates are the alkali metal and especially the sodium salts of the sulfuric acid half-esters derived from the $C_{12}$-$C_{18}$ fatty alcohols, for example from coconut butter alcohol, tallow alcohol, lauryl, myristyl, cetyl or stearyl alcohol or from $C_{10}$-$C_{20}$ Oxo alcohols and those half-esters of secondary alcohols of these chain lengths. The $C_{12}$-$C_{16}$ alkyl sulfates and $C_{12}$-$C_{15}$ alkyl sulfates as well as $C_{14}$-$C_{15}$ alkyl sulfates are preferred on the grounds of washing performance. 2,3-Alkyl sulfates are also suitable anionic surfactants.

Sulfuric acid mono-esters derived from straight-chained or branched $C_{7-21}$ alcohols ethoxylated with 1 to 6 moles ethylene oxide are also suitable, for example 2-methyl-branched alcohols with an average of 3.5 moles ethylene oxide (EO) or $C_{12-18}$ fatty alcohols with 1 to 4 EO.

Soaps are also preferred anionic surfactants. Saturated and unsaturated fatty acid soaps are suitable, such as the salts of lauric acid, myristic acid, palmitic acid, stearic acid, (hydrogenated) erucic acid and behenic acid, and especially soap mixtures derived from natural fatty acids such as coconut oil fatty acid, palm kernel oil fatty acid, olive oil fatty acid or tallow fatty acid.

The anionic surfactants, including the soaps, can be present in the form of their sodium, potassium or magnesium or ammonium salts. The anionic surfactants are preferably present in the form of their sodium salts. Further preferred counter ions for the anionic surfactants are also the protonated forms of choline, triethylamine or methylethylamine.

The anionic surfactant content of a surfactant preparation can be 1 to 40 wt %, preferably 5 to 30 wt % and quite particularly preferably 10 to 25 wt %, each based on the total surfactant preparation.

In another embodiment, the surfactant preparation is wherein it additionally contains at least one additional ingredient that is selected from the group consisting of builder, non-aqueous solvent, acid, water-soluble salt, thickener, disinfecting ingredient as well as combinations thereof.

The incorporation of one or more of the additional ingredients proves to be advantageous as in this way a further improved cleaning power and/or disinfection is achieved.

The improved cleaning power and/or disinfection is preferably based on a synergistic interaction of at least two ingredients. Such a synergy can be achieved particularly by the combination of the hydrolytic enzyme, preferably a protease, with one of the following described builders and/or with one of the following described non-aqueous solvents and/or with one of the following described acids and/or with one of the following described water-soluble salts and/or with one of the following described thickeners and/or with one of the following described disinfecting ingredients.

Silicates, aluminum silicates (particularly zeolites), carbonates, salts of organic di- and polycarboxylic acids as well as mixtures of these materials can be particularly cited as builders that can be comprised in the surfactant preparation.

Organic builders that can be present in the surfactant preparation are, for example, the polycarboxylic acids usable in the form of their sodium salts, polycarboxylic acids in this context being understood to be carboxylic acids that carry more than one acid function. These include, for example, citric acid, adipic acid, succinic acid, glutaric acid, malic acid, tartaric acid, maleic acid, fumaric acid, sugar acids, amino carboxylic acids, nitrilotriacetic acid (NTA), methylglycine diacetic acid (MGDA) and their derivatives and mixtures thereof. Preferred salts are the salts of polycarboxylic acids such as citric acid, adipic acid, succinic acid, glutaric acid, tartaric acid, sugar acids and mixtures thereof.

Polymeric polycarboxylates are also suitable as builders. These are for example the alkali metal salts of polyacrylic acid or polymethacrylic acid, for example those with a relative molecular mass of 600 to 750 000 g/mol.

Particularly suitable polymers are polyacrylates, which preferably have a molecular mass of 1000 to 15 000 g/mol. By virtue of their superior solubility, preferred representatives of this group can again be the short-chain polyacrylates, which have molecular weights of 1000 to 10 000 g/mol and particularly preferably 1000 to 5000 g/mol.

Further suitable copolymeric polycarboxylates are particularly those of acrylic acid with methacrylic acid and of acrylic acid or methacrylic acid with maleic acid. In order to improve the water solubility, the polymers can also comprise allyl sulfonic acids as the monomer, such as allyloxybenzene sulfonic acid and methallyl sulfonic acid.

Preferably however, soluble builders, such as for example citric acid, or acrylic polymers with a molecular mass of 1000 to 5000 g/mol, are preferably incorporated in the liquid surfactant preparation.

The molecular masses mentioned for polymeric polycarboxylates in the context of this specification are weight-average molecular weights Mw of the particular acid form which were fundamentally determined by means of gel permeation chromatography (GPC) using a UV detector. The measurement was carried out against an external polyacrylic acid standard, which provides realistic molecular weight values by virtue of its structural similarity to the investigated polymers. These values differ significantly from the molecular weights measured against polystyrene sulfonic acids as the standard. The molecular masses measured against polystyrene sulfonic acids are generally significantly higher than the molecular masses mentioned in this specification.

These types of organic builders can be comprised as desired in amounts of up to 40 wt %, particularly up to 25 wt % and preferably from 1 wt % to 8 wt %. Amounts close to the cited upper limit are preferably incorporated in pasty or liquid, particularly aqueous, surfactant preparations.

The surfactant preparations according to the invention are liquid and preferably comprise water as the main solvent. In addition or alternatively, non-aqueous solvents can be added to the surfactant preparation. Suitable non-aqueous solvents include monohydric or polyhydric alcohols, alkanolamines or glycol ethers, in so far that they are miscible with water in the defined concentration range. The solvents are preferably selected from ethanol, n-propanol, i-propanol, butanols, glycol, propane diol, butane diol, glycerin, diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol monomethyl ether, dipropylene glycol monoethyl ether, di-isopropylene glycol monomethyl ether, di-isopropylene glycol monoethyl ether, methoxytriglycol, ethoxytriglycol, butoxytriglycol, 1-butoxyethoxy-2-propanol, 3-methyl-3-methoxybutanol, propylene glycol t-butyl ether, di-n-octyl ether as well as mixtures of these solvents. However, it is preferred that the surfactant preparation comprises a polyol as the non-aqueous solvent. In particular, the polyol can include glycerin, 1,2-propane diol, 1,3-propane diol, ethylene glycol, diethylene glycol and/or dipropylene glycol. The surfactant preparation particularly preferably comprises a mixture of a polyol and a monohydric alcohol. Non-aqueous solvents can be incorporated in the surfactant preparation in amounts between 0.5 and 15 wt %, preferably, however below 12 wt %.

A pH resulting from mixing the usual components can be adjusted to a desired level, in that the surfactant preparations can comprise acids that are compatible with the system and the environment, particularly citric acid, acetic acid, tartaric acid, malic acid, glycolic acid, succinic acid, glutaric acid and/or adipic acid, and also mineral acids, particularly sulfuric acid or bases, particularly ammonium hydroxide or alkali metal hydroxides. These types of pH adjustors are preferably comprised in the surfactant preparations in amounts of not more than 20 wt %, in particular from 1.2 wt % to 17 wt %.

In the context of the invention, a surfactant preparation can additionally comprise one or more water-soluble salts that serve, for example, to adjust the viscosity. In this regard they can be inorganic or organic salts. Here, inorganic salts that can be incorporated are preferably selected from the group that includes colorless water-soluble halides, sulfates, sulfites, carbonates, hydrogen carbonates, nitrates, nitrites, phosphates and/or oxides of the alkali metals, of the alkaline earth metals, of aluminum and/or of transition metals; in addition, ammonium salts can be incorporated. In this regard, halides and sulfates of the alkali metals are particularly preferred; consequently the inorganic salt is preferably selected from the group that includes sodium chloride, potassium chloride, sodium sulfate, potassium sulfate as well as their mixtures. Exemplary organic salts that can be incorporated are colorless water-soluble alkali metal, alkaline earth metal, ammonium, aluminum and/or transition metal salts of carboxylic acids. The salts are preferably selected from the group that includes formate, acetate, propionate, citrate, malate, tartrate, succinate, malonate, oxalate, lactate as well as mixtures thereof.

A surfactant preparation according to the invention can comprise one or more thickeners to thicken it. The thickener is preferably selected from the group that includes xanthan, guar, carrageenan, agar agar, gellan, pectin, locust bean flour and mixtures thereof. These compounds are also effective thickeners in the presence of inorganic salts. In a particularly preferred embodiment, the surfactant preparation comprises xanthan as the thickener, as xanthan thickens effectively even in the presence of high salt concentrations and prevents a macroscopic separation of the continuous phase. In addition, the thickener stabilizes the continuous surfactant-poor phase and prevents a macroscopic phase separation.

Alternatively, (meth)acrylic acid (co)polymers can also be employed as the thickener. Exemplary suitable acrylic and methacrylic (co)polymers include the high molecular weight homopolymers of acrylic acid, crosslinked with a polyalkenyl polyether, in particular an allyl ether of saccharose, pentaerythritol or propylene (INCI name according to the "International Dictionary of Cosmetic Ingredients" of "The Cosmetic, Toiletry and Fragrance Association (CTFA)": Carbomer), which are also called carboxyvinyl polymers. Polyacrylic acids of this type are available inter alia under the trade names Polygel® and Carbopol®. In addition, the following acrylic acid copolymers are suitable, for example: (i) copolymers of two or more monomers of the group of the acrylic acid, methacrylic acid and their simple esters, preferably formed with $C_{1-4}$ alkanols (INCI Acrylates Copolymer), which are available for example under the trade names Aculyn®, Acusol® or Tego® Polymer; (ii) crosslinked high molecular weight acrylic acid copolymers, to which belong for example the copolymers of $C_{10-30}$ alkyl acrylates with one or more monomers of the group of acrylic acid, methacrylic acid and their simple esters, preferably formed with $C_{1-4}$ alkanols, crosslinked with an allyl ether of saccharose or of pentaerythritol (INCI Acrylates/C10-30 Alkyl Acrylate Crosspolymer) and which are available under the trade name Carbopol®. Further suitable polymers are (meth)acrylic acid (co)polymers of the Sokalan® type.

It can be preferred that the surfactant preparation according to the invention comprises a (meth)acrylic acid (co) polymer in combination with another thickener, preferably xanthan. The surfactant preparation can comprise 0.05 to 1.5 wt % and preferably 0.1 to 1 wt % thickener, each based on the total surfactant preparation. The amount of added thickener depends in this regard on the type of thickener and the desired degree of thickening.

A disinfecting ingredient is particularly understood to mean ingredients that possess an antimicrobial or antiviral activity, i.e. kill germs. In this regard, the germ-killing effect depends on the content of the disinfecting ingredient in the surfactant preparation, wherein the germ-killing activity decreases with decreasing contents of disinfecting ingredient or increasing dilution of the surfactant preparation.

A preferred disinfecting ingredient is ethanol or propanol. Due to their solvent properties and their germicidal action these monohydric alcohols are often generally employed in disinfectants and also in cleaning agents. In this regard, the term "propanol" includes both 1-propanol (n-propanol) as well as 2-propanol ("isopropanol"). Ethanol and/or propanol is/are comprised for example in an amount totaling 10 to 65 wt %, preferably 25 to 55 wt % in the surfactant preparation. Another preferred disinfecting ingredient is tea tree oil. Here it concerns the ethereal oil of the Australian tea tree (*Melaleuca alternifolia*), an evergreen shrub of the genus *Melaleuca*, indigenous to New South Wales and Queensland, as well other tea tree types from various genera (e.g. *Baecka*, *Kunzea* and *Leptospermum*) in the family of the Myrtaceae). The tea tree oil is obtained by steam distillation of the leaves and branch tips of this tree and is a mixture of ca. 100 substances; the major constituents include (+)-terpinen-4-ol, α-terpinenes, terpinols, terpineol, pinene, myrcene, phellandrene, p-cymene, limonene and 1,8-cineol. Tea tree oil is comprised for example in an amount of 0.05 to 10 wt %, preferably 0.1 to 5 wt %, in the virucidal treatment solution. Another preferred disinfecting ingredient is lactic acid. Lactic acid or 2-hydroxypropionic acid is a fermentation product that is produced from various microorganisms. It is weakly antibiotically active. Lactic acid is comprised for example in amounts of up to 10 wt %, preferably 0.2 to 5.0 wt % in the surfactant preparation.

Additional disinfecting ingredients are for example active substances from the groups of the alcohols, aldehydes, antimicrobial acids or their salts, carboxylic acid esters, acid amides, phenols, phenol derivatives, diphenyls, diphenylalkanes, urea derivatives, oxygen and nitrogen acetals and formals, benzamidines, isothiazoles and their derivatives such as isothiazolines and isothiazolinones, phthalimide derivatives, pyridine derivatives, antimicrobial surface-active compounds, guanidines, antimicrobial amphoteric compounds, quinolines, 1,2-dibromo-2,4-dicyanobutane, iodo-2-propinyl butyl carbamate, iodine, iodophores and peroxides. Among these, preferred active substances are preferably selected from the group that includes 1,3-butane diol, phenoxyethanol, 1,2-propylene glycol, glycerin, undecylenic acid, citric acid, lactic acid, benzoic acid, salicylic acid, thymol, 2-benzyl-4-chlorophenol, 2,2'-methylene-bis-(6-bromo-4-chlorophenol), 2,4,4'-trichloro-2'-hydroxydiphenyl ether, N-(4-chlorophenyl)-N-(3,4-dichlorophenyl)-urea, N,N'-(1,10-decanediyldi-1-pyridinyl-4-ylidene)-bis-(1-octanamine) dihydrochloride, N,N'-bis-(4-chlorophenyl)-3,12-diimino-2,4,11,13-tetraazatetradecanediimide amide, quaternary surface active compounds, guanidine. Preferred surface active quaternary compounds comprise an ammonium, sulfonium, phosphonium, iodonium or arsonium group. Furthermore, disinfecting ethereal oils can also be incorporated and provide a fragrance to the virucidal treatment solution. However, particularly preferred active substances are selected from the group comprising salicylic acid, quaternary surfactants, especially benzalkonium chloride, peroxy compounds, especially hydrogen peroxide, alkali metal hypochlorite as well as mixtures thereof. Such an additional disinfecting ingredient is comprised for example in an amount of 0.01 to 1 wt %, preferably 0.02 to 0.8 wt %, particularly 0.05 to 0.5 wt %, particularly preferably 0.1 to 0.3 wt %, most preferably 0.2 wt % in the surfactant preparation.

Liquid surfactant preparations according to the invention which are in the form of solutions in standard solvents are generally prepared by a simple mixing of the ingredients, which can be added as is or as a solution into an automatic mixer.

In another preferred embodiment of the invention, a method according to the invention is wherein the component that stabilizes the hydrolytic enzyme is essentially free of boric acid or has a boron content of less than 50%, 45%, 40%, 35%, 30%, 25%, 20%, 15%, 10% or 5%, based on the total amount of the component that stabilizes the hydrolytic enzyme. The component that stabilizes the hydrolytic enzyme is quite particularly preferably boron-free.

In another preferred embodiment of the invention, a method according to the invention is wherein the component that stabilizes the hydrolytic enzyme contains a reversible protease inhibitor that is selected from a) monosaccharide glycerate, in particular an aldose glycerate, a hemiacetal of an aldose glycerate, a ketose glycerate or a hemiketal of a ketose glycerate, especially wherein the monosaccharide in the monosaccharide glycerate
   a. is a triose residue, in particular glyceraldehyde or dihydroxyacetone, or
   b. is a tetrose residue, in particular erythrose, threose or erythrulose, or
   c. is a pentose residue, in particular ribose, arabinose, xylose, lyxose, desoxyribose, ribulose or xylulose, or
   d. is a hexose residue, in particular allose, altrose, glucose, mannose, gulose, idose, galactose, talose, fucose, rhamnose, chinovose or fructose;

b) oligoaminobiphenyl oligocarboxylic acids, in particular a diaminobiphenyl dicarboxylic acid, in particular 3,3-diamino[1,1-biphenyl]-2,4-dicarboxylic acid;

c) aminophthalic acid, in particular 4-aminophthalic acid;

d) phthaloyl glutamic acid;
e) polysubstituted benzoic acid that has a carboxyl group on at least two carbon atoms of the benzene ring, in particular a polysubstituted benzoic acid that is a benzoic acid with four carboxylic groups on the benzene ring, in particular pyromellitic acid;
f) phenylalkyl dicarboxylic acids, in particular phenylmalonic acid or benzylmalonic acid;
g) polyols, in particular glycerin, 1,2-ethylene glycol, 1,2-propylene glycol or 1,3-propylene glycol;
h) antioxidant or glyceric acid;
i) calcium compound, lactate or a lactate derivative;
j) boric acid;
k) phenylboronic acid derivative with the structural formula

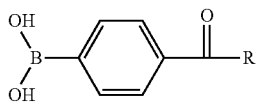

in which R stands for hydrogen, a hydroxy, a C1-C6 alkyl, a substituted C1-C6 alkyl, a C1-C6 alkenyl or a substituted C1-C6 alkenyl group, preferably 4-formylphenylboronic acid (4-FPBA);
l) mono or poly-substituted phenylboronic acid that has a hydroxy group on at least one carbon atom of the phenyl ring, in particular a phenylboronic acid that has a hydroxy group on at least one carbon atom of the phenyl ring, in particular wherein the substituents on the other carbon atoms of the phenyl ring are —H, in particular a hydroxyphenylboronic acid, preferably 3-hydroxyphenylboronic acid (3-HPBA).

The component that stabilizes the hydrolytic enzyme can contain a monosaccharide glycerate as the reversible inhibitor. This is understood to mean a substance, in which a monosaccharide residue is covalently bonded to a glycerate residue through an acetal linkage. In the context of the present invention, a monosaccharide glycerate is consequently described by the following Formula (I):

wherein R is a monosaccharide residue.

In the context of the present invention, a monosaccharide is a product of the partial oxidation of a polyhydric alcohol. A monosaccharide possesses a chain of at least three carbon atoms as the backbone and has a carbonyl group as well as at least one hydroxy group. Trioses (3), tetroses (4), pentoses (5), hexoses (6), heptoses (7) etc. are differentiated by the number of carbon atoms. In principle the length of the carbon chain is unlimited; preferably the carbon chain has between three and nine carbon atoms.

Moreover, the monosaccharide can be in acyclic form (non-cyclic) or cyclic form. A double bonded oxygen atom is present on one of the carbon atoms of the acyclic form, such that a carbonyl group is present. If this carbonyl group is located at the terminal position of the carbon chain, then there exists an aldehyde group and the monosaccharide is an aldose. If the carbonyl group is located within the carbon chain, then there exists a keto group and the monosaccharide is a ketose. The cyclic monosaccharides are hemiacetals or hemiketals derived from the corresponding aldoses or ketoses. These types of monosaccharides are preferably furanoses (five-membered rings) or pyranoses (six-membered rings) each with an oxygen atom in the ring that can each be in the α- or β-configuration.

The monosaccharide can also exist in any possible stereoisomeric form. Due to the spatial arrangement of the hydroxy groups of the monosaccharide, the monosaccharide can be in the D- or L-configuration, wherein the configuration is determined in a standard manner by means of the Fischer projection of the monosaccharide, in which the C—C bonds are represented as extended in the notional (thermodynamically unfavourable) ecliptic position vertically above one another in the plane of the paper, and the substituents (here hydrogen atoms and hydroxy groups) are presented on the right or left depending on the configuration, yielding an unequivocal configuration. The chiral carbon atom located farthest from the anomeric carbon atom produces the D configuration in the right position, and the L configuration in the left position.

Preferred monosaccharides correspond to the general empirical formula $C_nH_{2n}O_n$, where n is a number between three and nine, preferably between four and six, and particularly preferably is six.

Also included among the monosaccharides are derivatives of these compounds that do not conform to the aforementioned general empirical formula. Such derivatives comprise further chemical modifications; in particular, they can contain one or more methyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, 2,2,5,7,8-pentamethylchroman-6-sulfonyl residues, or combinations thereof. For example, D-glucuronic acid (6-carboxy-D-glucose), D-galacturonic acid (6-carboxy-D-galactose), N-acetyl-D-glucosamine (also N-acetylchitosamine), D-glucosamine (also chitosamine), N-acetyl-D-galactosamine (also N-acetylchondrosamine), or D- and L-fucose (6-deoxy-D- and L-galactose) are monosaccharides in the context of the present invention.

The monosaccharide glycerate is preferably an aldose glycerate, a hemiacetal of an aldose glycerate, a ketose glycerate or a hemiketal of a ketose glycerate.

The monosaccharide in the monosaccharide glycerate is particularly preferably
a) a triose residue, in particular glyceraldehyde or dihydroxyacetone, or
b) a tetrose residue, in particular erythrose, threose or erythrulose, or
c) a pentose residue, in particular ribose, arabinose, xylose, lyxose, desoxyribose, ribulose or xylulose, or
d) a hexose residue, in particular allose, altrose, glucose, mannose, gulose, idose, galactose, talose, fucose, rhamnose, chinovose or fructose.

Monosaccharide glycerates of this kind are particularly effective as compounds that are provided in the context of the present invention as the component that stabilizes the hydrolytic enzyme. In a particularly preferred embodiment of the invention, the monosaccharide glycerate is glucosyl glycerate. A particularly preferred glucosyl glycerate is indicated in Formula (II) below:

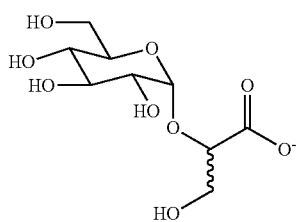

(II)

The component that stabilizes the hydrolytic enzyme can contain an oligoaminobiphenyl oligocarboxylic acid as the reversible inhibitor, in particular a diaminobiphenyl dicarboxylic acid, in particular 3,3-diamino[1,1-biphenyl]-2,4-dicarboxylic acid.

In the context of the present invention, an olgoaminobiphenyl oligocarboxylic acid is described by Formula (III) below:

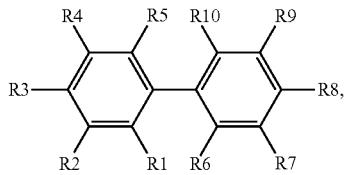

(III)

wherein R1, R2, R3, R4, R5, R6, R7, R8, R9 and R10 are each —$NH_2$, —COOH or —H, wherein at least two of the R1 to R10 groups are —$NH_2$ and at least two of the R1 to R10 groups are —COOH and the other groups are —H. Preferably, those R1 to R10 groups that are —$NH_2$, and those R1 to R10 groups that are —COOH, are located on neighboring carbon atoms, i.e. ortho to one another.

More preferably, exactly two of the R1 to R10 groups are —$NH_2$ and two of the R1 to R10 groups are —COOH and the other groups are —H. Such an embodiment of the invention is consequently wherein the oligoaminobiphenyl oligocarboxylic acid is a diaminobiphenyl dicarboxylic acid. Particularly preferably, R1 is —COOH, R2-$NH_2$, R7-$NH_2$, R8-COOH, and R3, R4, R5, R6, R9, R10 are each —H. In such a particularly preferred embodiment of the invention, the oligoaminobiphenyl oligocarboxylic acid is 3,3-diamino[1,1-biphenyl]-2,4-dicarboxylic acid, which is depicted in the Formula (IV) below:

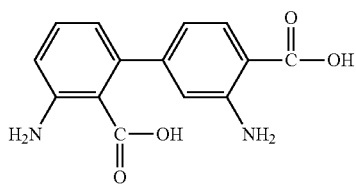

(IV)

In the context of the invention, an oligoaminobiphenyl oligocarboxylic acid includes further derivatives of this compound. Such derivatives comprise further chemical modifications; in particular, one or more of the amino groups can be glycosylated, oxidized, N-methylated, N-formylated, N-acetylated or they can comprise one or more methyl, amino, nitro, chloro, fluoro, bromo, hydroxy, carboxyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, 2,2,5,7,8-pentamethylchroman-6-sulfonyl residues or groups or combinations thereof.

The component that stabilizes the hydrolytic enzyme can contain aminophthalic acid as the reversible inhibitor, especially 4-aminophthalic acid.

This is understood to mean a benzene dicarboxylic acid that has an $NH_2$ group at at least one other position of the phenyl ring. The two carboxylic groups of the benzene dicarboxylic acid can be ortho, meta or para to one another. They are preferably ortho to one another. The —$NH_2$ group is located on one of the carbon atoms of the phenyl ring on which no carboxylic group is located. The substituents on the remaining positions of the phenyl ring are preferably —H.

A preferred compound of this type is depicted by the following Formula (V):

(V):

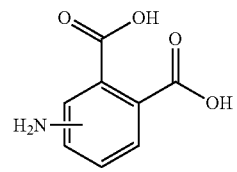

Here, the —$NH_2$ group is located on the C3 or C4 carbon atom of the phenyl ring, particularly preferably on C4 of the phenyl ring.

In the context of the invention, other derivatives of this compound count as an aminophthalic acid. Such derivatives possess further chemical modifications; in particular, the amino group can be glycosylated, oxidized, N-methylated, N-formylated or N-acetylated. Alternatively or in addition they can comprise one or more methyl, amino, nitro, chloro, fluoro, bromo, hydroxy, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, 2,2,5,7,8-pentamethylchroman-6-sulfonyl residues or groups or combinations thereof.

The component that stabilizes the hydrolytic enzyme can contain phthaloylglutamic acid as the reversible inhibitor.

This is understood to mean a substance that is depicted by the Formula (VI) below (N-phthaloyl-L-glutamic acid):

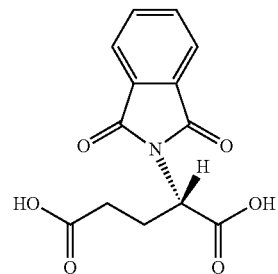

(VI)

Alternatively or in addition, the component that stabilizes the hydrolytic enzyme can contain a phthaloyl aspartic acid as the reversible inhibitor. This is understood to mean a substance that is depicted by the Formula (VII) below (N-phthaloyl-L-aspartic acid):

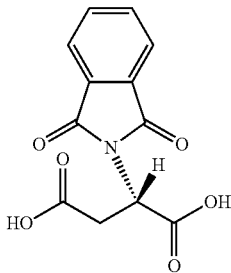

(VII)

In the context of the invention, other derivatives of these compounds count as a phthaloyl glutamic acid or phthaloyl aspartic acid. Such derivatives comprise further chemical modifications; in particular they can be glycosylated, or they can comprise on the phthaloyl group one or more methyl, amino, nitro, chloro, fluoro, bromo, hydroxy, carboxyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyoxycarbonyl, triphenylmethyl, 2,2,5,7,8-pentamethylchroman-6-sulfonyl residues or groups or combinations thereof.

The component that stabilizes the hydrolytic enzyme can contain a polysubstituted benzoic acid as the reversible inhibitor.

This is understood to mean a benzoic acid that possesses a carboxylic group (—COOH group) on at least two carbon atoms of the benzene ring. The benzoic acid preferably possesses three, four, five or six carboxylic groups on the benzene ring. More preferably, the benzoic acid possesses a hydrogen on those carbon atoms that do not carry carboxylic groups.

The carboxylic groups of the disubstituted benzoic acids can be ortho, meta or para to one another. Additional carboxylic groups can be on any intermediate carbon atoms.

The polysubstituted benzoic acid particularly preferably concerns a benzoic acid with four carboxylic groups on the benzene ring. The carboxylic groups are quite particularly preferably located on the C1, C2, C4 and C5 carbon atoms of the benzene ring. Pyromellitic acid is such a compound. It has carboxylic groups on the C1, C2, C4 and C5 carbon atoms of the benzene ring and hydrogen on the C3 and C6 carbon atoms and depicts a quite particularly preferred development of the component that stabilizes the hydrolytic enzyme. It is illustrated in Formula (VIII) below:

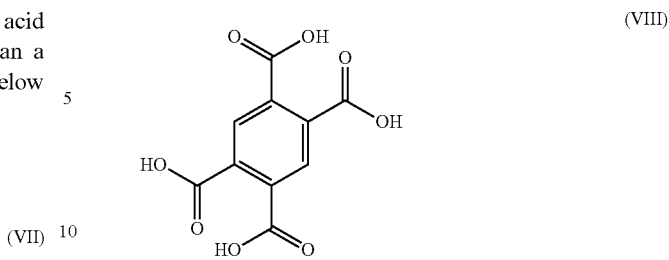

(VIII)

In the context of the invention, other derivatives of this compound also count as a polysubstituted benzoic acid. Such derivatives possess further chemical modifications; in particular, they can comprise one or more methyl, amino, nitro, chloro, fluoro, bromo, hydroxy, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyoxycarbonyl, triphenylmethyl, 2,2,5,7,8-pentamethylchroman-6-sulfonyl residues or groups or combinations thereof.

The component that stabilizes the hydrolytic enzyme can contain phenylalkyl dicarboxylic acid as the reversible inhibitor, especially phenylmalonic acid.

In the context of the present invention, a phenylmalonic acid is depicted by Formula (IX) below:

$$C_6H_5\text{—}(CH_2)_n\text{—}CH(COOH)_2, \quad (IX)$$

wherein n is a whole number between 0 and 14 and increasingly preferably between 0 and 10, between 0 and 5, between 0 and 4, between 0 and 3, between 0 and 2 and quite particularly preferably is 0 or 1. Consequently, particularly preferred developments of the invention are wherein the phenylalkyl dicarboxylic acid is phenylmalonic acid or benzylmalonic acid.

Phenylmalonic acid is depicted in Formula X) below, benzylmalonic acid in Formula (XI) below:

(X):

$C_6H_5CH(COOH)_2$ (XI):

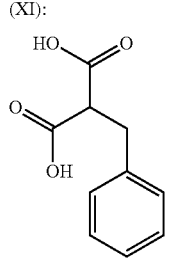

In the context of the invention, other derivatives of this compound count as a phenylalkyl carboxylic acid. Such derivatives possess further chemical modifications; in particular they can be glycosylated or oxidized or they can comprise on the phenyl ring one or more methyl, amino, nitro, chloro, fluoro, bromo, hydroxy, carboxyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyoxycarbonyl, triphenylmethyl, 2,2,5,7,8-pentamethylchroman-6-sulfonyl residues or groups or combinations thereof.

The component that stabilizes the hydrolytic enzyme can moreover contain a polyol as the reversible inhibitor, especially glycerin, 1,2-ethylene glycol, 1,2-propylene glycol or 1,3-propylene glycol. The component that stabilizes the hydrolytic enzyme can moreover contain an antioxidant or glyceric acid, a calcium compound, lactate or a lactate derivative. The component that stabilizes the hydrolytic enzyme can moreover contain boric acid as the reversible inhibitor.

The component that stabilizes the hydrolytic enzyme can moreover contain a phenylboronic acid derivative as the reversible inhibitor with the structural formula

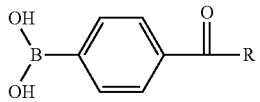

in which R stands for hydrogen, a hydroxy, a C1-C6 alkyl, a substituted C1-C6 alkyl, a C1-C6 alkenyl or a substituted C1-C6 alkenyl group, preferably 4-formylphenylboronic acid (4-FPBA).

The component that stabilizes the hydrolytic enzyme can moreover contain as the reversible inhibitor a mono or poly-substituted phenylboronic acid that has a hydroxy group on at least one carbon atom of the phenyl ring, in particular a phenylboronic acid that has a hydroxy group on at least one carbon atom of the phenyl ring, in particular wherein the substituents on the other carbon atoms of the phenyl ring are —H. Particularly preferably it concerns a hydroxyphenylboronic acid, quite particularly preferably 3-hydroxyphenylboronic acid (3-HPBA). It is described by the following Formula (XII):

(XII):

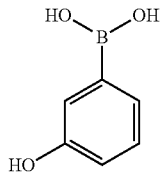

In the context of the present invention, all compounds that are provided as the component that stabilizes the hydrolytic enzyme can be present in all protonated or deprotonated forms. Further, all such compounds, particularly their deprotonated forms, can be accompanied by cations. In this regard, preferred cations are divalent cations, especially Ca-ions ($Ca^{2+}$), Mg-ions ($Mg^{2+}$) and Zn-ions ($Zn^{2+}$). Ca-ions ($Ca^{2+}$) are particularly preferred. In addition, the compounds can be present in all possible stereoisomeric forms.

Another subject matter of the invention are hydrolytic enzymes that can be obtained by a method according to the invention as described above. Preferred hydrolytic enzymes are proteases and amylases, especially proteases. Further preferred hydrolytic enzymes are selected from the group consisting of a) protease with an amino acid sequence that over its whole length is at least 90% identical to SEQ ID NO: 3 and has the amino acid substitution S166A in the count according to SEQ ID NO: 1;

b) protease with an amino acid sequence that over its whole length is at least 90% identical to SEQ ID NO: 3 and has the amino acid substitution S166V in the count according to SEQ ID NO: 1;

c) protease with an amino acid sequence that over its whole length is at least 90% identical to SEQ ID NO: 3 and has the amino acid substitution S166Y in the count according to SEQ ID NO: 1;

d) protease with an amino acid sequence that over its whole length is at least 90% identical to SEQ ID NO: 3 and has the amino acid substitution S166G in the count according to SEQ ID NO: 1;

e) protease with an amino acid sequence that over its whole length is at least 90% identical to SEQ ID NO: 3 and has the amino acid substitution A187D in the count according to SEQ ID NO: 1;

f) protease with an amino acid sequence that over its whole length is at least 90% identical to SEQ ID NO: 3 and has the amino acid substitution F189R in the count according to SEQ ID NO: 1;

g) protease with an amino acid sequence that over its whole length is at least 90% identical to SEQ ID NO: 3 and has the amino acid substitution Q191R in the count according to SEQ ID NO: 1;

h) protease with an amino acid sequence that over its whole length is at least 90% identical to SEQ ID NO: 3 and has the amino acid substitutions 5166G and Q191R in the count according to SEQ ID NO: 1;

i) protease with an amino acid sequence that over its whole length is at least 90% identical to SEQ ID NO: 3 and has the amino acid substitutions A187D and F189R in the count according to SEQ ID NO: 1.

The identity value, in particular the identity value of 100%, refers here to the respective protease without the stipulated substitution(s), i.e. to the basic structure (basic sequence) of the protease. The substitutions as listed in each case are then to be introduced into this respective basic structure. For example a protease with an amino acid sequence that over its whole length is at least 100% identical to SEQ ID NO: 3 and has the amino acid substitution S166A in the count according to SEQ ID NO: 1, is a protease according to SEQ ID NO: 3 with the amino acid substitution S166A (in the counting method according to SEQ ID NO: 1). The same applies for the other proteases.

In another preferred embodiment, the above-mentioned proteases have only the respectively listed amino acid substitution or the respectively listed amino acid substitutions.

In another preferred embodiment, the hydrolytic enzyme is wherein it has a reduced relative activity compared to the relative activity of the starting enzyme towards the reversible inhibitor, in particular towards one of the reversible inhibitors as listed above. The hydrolytic enzyme is preferably a protease or an amylase, in particular a protease and quite particularly preferably a protease as described above. Further preferred developments of these proteases are characterized in that the a) protease according to a) has a reduced relative activity in comparison to the relative activity of a protease according to SEQ ID NO: 3 towards boric acid, 4-formylphenylboronic acid (4-FPBA) or 3-hydroxyphenylboronic acid (3-HPBA), in particular 4-formylphenylboronic acid (4-FPBA);

b) protease according to b) has a reduced relative activity in comparison to the relative activity of a protease according to SEQ ID NO: 3 towards boric acid, 4-formylphenylboronic acid (4-FPBA) or 3-hydroxyphenylboronic acid (3-HPBA), in particular 3-hydroxyphenylboronic acid (3-HPBA);

c) protease according to c) has a reduced relative activity in comparison to the relative activity of a protease according to SEQ ID NO: 3 towards boric acid or 3-hydroxyphenylboronic acid (3-HPBA), in particular 3-hydroxyphenylboronic acid (3-HPBA);

d) protease according to d) has a reduced relative activity in comparison to the relative activity of a protease according to SEQ ID NO: 3 towards boric acid;

e) protease according to e) has a reduced relative activity in comparison to the relative activity of a protease according to SEQ ID NO: 3 towards boric acid;

f) protease according to 0 has a reduced relative activity in comparison to the relative activity of a protease according to SEQ ID NO: 3 towards boric acid or benzylmalonic acid, in particular boric acid;

g) protease according to g) has a reduced relative activity in comparison to the relative activity of a protease according to SEQ ID NO: 3 towards boric acid or benzylmalonic acid, in particular benzylmalonic acid;

h) protease according to h) has a reduced relative activity in comparison to the relative activity of a protease according to SEQ ID NO: 3 towards boric acid or benzylmalonic acid, in particular benzylmalonic acid;

i) protease according to i) has a reduced relative activity in comparison to the relative activity of a protease according to SEQ ID NO: 3 towards boric acid or benzylmalonic acid, in particular benzylmalonic acid.

In this regard, the relative activities are preferably determined as in Example 1.

EXAMPLES

Example 1

Adapting a Protease to Given Compounds that Inhibit and Thus Stabilize the Protease All molecular-biological work was carried out by standard methods as can be found, for example, in the manual by Fritsch, Sambrook and Maniatis "Molecular cloning: a laboratory manual", Cold Spring Harbour Laboratory Press, New York, 1989, or comparable specialist literature. Enzymes and kits were used according to the directions of the relevant manufacturer.

A protease according to SEQ ID NO: 3 was used as the hydrolytic enzyme (starting enzyme). Furthermore, the following listed reversible protein inhibitors were each provided as the component that stabilizes the hydrolytic enzyme:
1. Boric acid
2. 4-Formylphenylboronic acid (4-FPBA)
3. 3-Hydroxyphenylboronic acid (3-HPBA)
4. Benzylmalonic acid (BMA)

The nucleic acid sequence of the hydrolytic enzyme present on a plasmid was modified individually or in combination as indicated in Tables 1 and 2 using site directed mutagenesis by means of specific, adapted primers using a Phusion Hot Start Polymerase at the positions S166, A187, F189 or Q191 in the counting according to SEQ ID NO: 1, and the resulting variants were transformed into a suitable host. Active clones were selected by means of a protease-sensitive medium and the DNA sequence was sequenced after isolation of the plasmid for identification purposes. The modified proteases were expressed in the Bacillus host and prepared for the activity determination.

The activity was determined in a liquid preparation that was constituted as follows (all data in wt %): 0.3-0.5% xanthan, 0.2-0.4% defoamer, 6-7% glycerin, 0.3-0.5% ethanol, 4-7% FAEOS (fatty alcohol ether sulfate), 24-28% non-ionic surfactants, 1-2% sodium citrate (dihydrate), 2-4% soda, 14-16% cocoanut fatty acids, 0.5% HEDP (1-hydroxyethane-(1,1-diphosphonic acid)), 0-0.4% PVP (polyvinyl pyrrolidone) 0-0.5% optical brightener, 0-0.001% % colorant, the remainder being demineralized water.

To a 50% conc. liquid preparation of the liquid surfactant preparation were added 0.92 mM AAPF. The reversible inhibitor to be tested was also comprised in the required amount to inhibit the starting enzyme by 20-40%. 20 μl of the respective protease (starting enzyme as well as modified protease variants) were added and the proteolytic activity determined from the release of the chromophore para-nitroaniline (pNA) from the substrate suc-L-Ala-L-Ala-L-Pro-L-Phe-p-nitroanilide (suc-AAPF-pNA). The protease cleaves the substrate and releases pNA. The released pNA causes the extinction at 410 nm to increase; the change in extinction as a function of time is a measure of the enzymatic activity (see Del Mar et al., 1979). The measurement was carried out at a temperature of 25° C., at pH 8.6 and a wavelength of 410 nm.

The measured activity was compared with the activity of a reference formulation of the same protease sample without inhibitor and the respective relative activities of the modified proteases and the starting enzyme were determined. A greater reduction in the relative activity of a variant with the respective inhibitor than for the starting enzyme demonstrates a better inhibition. The results are presented in the following Tables 1 and 2 (the relative activities are each given).

TABLE 1

| Enzyme | Without inhibitor | Boric acid | 4-FPBA | 3-HPBA |
| --- | --- | --- | --- | --- |
| S166 | 100% | 83% | 75% | 83% |
| S166A | 100% | 76% | 61% | 83% |
| S166V | 100% | 59% | 71% | 53% |
| S166Y | 100% | 68% | 100% | 58% |

TABLE 2

| Enzyme | Without inhibitor | Boric acid | BMA |
| --- | --- | --- | --- |
| S166 | 100% | 79% | 81% |
| A187D | 100% | 47% | 79% |
| F189R | 100% | 53% | 80% |
| Q191R | 100% | 76% | 63% |
| S166G | 100% | 65% | 80% |
| S166G/Q191R | 100% | 57% | 35% |
| A187D/F189R | 100% | 37% | 43% |

It is clear that the proteases obtained by carrying out a method according to the invention are better adapted to the component that stabilizes the hydrolytic enzyme, in particular to the reversible inhibitor, and consequently are better inhibited or stabilized by them. An improved inhibition of the proteases obtained by carrying out a method according to the invention for the variants listed in Table 1 was also achieved with benzylmalonic acid (BMA) as the reversible inhibitor.

Example 2

Inhibition Measurements in the Biochemical Test

The variants S166V and S166G/Q191R as well as the starting enzyme according to SEQ ID NO: 3 were expressed in a suitable expression system, further purified by means of ion exchange chromatography and prepared for the activity determinations in 0.1 M Tris/HCl buffer pH 8.6, comprising Brij35. To the formulations were added increased amounts of the reversible inhibitor 3-HPBA or BMA (see Tables 3 and 4) and the proteolytic residual activity of the respective protease was determined from the release of the chromophore para-nitroaniline (pNA) from the substrate suc-L-Ala-L-Ala-L-Pro-L-Phe-p-nitroanilide (suc-AAPF-pNA) as described above. The obtained activities are shown in the Tables 3 and 4.

TABLE 3

| Enzyme | Without inhibitor | 3-HPBA (in mM) | | | | |
|---|---|---|---|---|---|---|
| | | 0.05 | 0.1 | 0.5 | 1 | 1.5 |
| Starting enzyme | 100% | 93% | 89% | 81% | 65% | 56% |
| S166V | 100% | 84% | 87% | 65% | 51% | 40% |

TABLE 4

| Enzyme | Without inhibitor | BMA (in Gew.-%) | | | | | | | |
|---|---|---|---|---|---|---|---|---|---|
| | | 0.05 | 0.5 | 1.0 | 1.7 | 2.5 | 3.3 | 4.0 | 5.0 |
| Starting enzyme | 100% | 96% | 95% | 93% | 94% | 74% | 73% | 78% | 64% |
| S166G/Q191R | 100% | 88% | 55% | 42% | 35% | 38% | 32% | 36% | 32% |

It is clear that the respective variant shows a stronger inhibition by the reversible inhibitor than the starting enzyme. Consequently, carrying out a method according to the invention afforded a variant that is better adapted to a given reversible inhibitor, here 3-HPBA or BMA.

Example 3

Determination of the Storage Stability in a Liquid Surfactant Preparation

The variants S166V and S166G/Q191R as well as the starting enzyme according to SEQ ID NO: 3 were added in equal concentration to reaction formulations that comprised a surfactant preparation as described in Example 1 as well as a reversible inhibitor in concentrations indicated in Table 5. The formulations were stored at 30° C. and the remaining proteolytic residual activity of the protease was determined at regular intervals from the release of the chromophore para-nitroaniline (pNA) from the substrate suc-L-Ala-L-Ala-L-Pro-L-Phe-p-nitroanilide (suc-AAPF-pNA) as described above. The addition of the inhibitors lead to the increased factors of the half-life times indicated in Table 5 (half-life with inhibitor divided by half-life without inhibitor).

TABLE 5

| Enzyme | Boric acid (in wt %) | | 3-HPBA (in wt %) | | BMA (in wt %) |
|---|---|---|---|---|---|
| | 1 | 0.25 | 0.02 | 0.005 | 1 |
| Starting enzyme | 26 | 4 | 14 | 5 | 3 |
| S166V | 43 | 6 | 34 | 9 | n.d. |
| S166G/Q191R | n.d. | n.d. | n.d. | n.d. | 5 |

(n.d.: not determined)

It is clear that the respective variant even in a surfactant preparation shows a stronger inhibition by the reversible inhibitor than the starting enzyme. Consequently, carrying out a method according to the invention afforded a variant that also in the context of a surfactant preparation is better adapted to a given reversible inhibitor, here besides boric acid, especially 3-HPBA and BMA.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for adapting a hydrolytic enzyme to a component that stabilizes the hydrolytic enzyme, comprising the process steps:
   a) providing a first reaction mix comprising a hydrolytic enzyme (starting enzyme) and a component that stabilizes the hydrolytic enzyme, said component comprising a reversible inhibitor of the hydrolytic enzyme having an inhibition constant ($K_i$) of 0.01 to 500 mM and is free of boric acid;
   b) providing a second reaction mix comprising a modified modifying the amino-acid sequence of the hydrolytic enzyme comprising at least one position by substitution, deletion or insertion;
   c) independently determining the relative activity of the enzyme from step b) and the relative activity of the starting enzyme in a liquid preparation, wherein the relative activity is determined by:
      (i) measuring the activity of each enzyme in the presence of the component that stabilizes the hydrolytic enzyme;
      (ii) measuring the activity of each enzyme in the absence of the component that stabilizes the hydrolytic enzyme;
      (iii) for each enzyme, dividing the measured activity of step i. by the measured activity of step (ii) and multiplying by 100; and
   d) selecting that enzyme that exhibits a diminished relative activity in comparison to the relative activity of the starting enzyme.

2. The method according to claim 1, wherein the hydrolytic enzyme is a protease, amylase, cellulase, glycosidase, hemicellulase, mannanase, xylanase, xyloglucanase, xanthanase, pectinase, β-glucosidase, carrageenase or a lipase or a mixture that comprises at least two of these enzymes.

3. The method according to claim 1, wherein the hydrolytic enzyme is a protease or an amylase, particularly a protease.

4. The method according to claim 3, wherein the protease is modified at a position that corresponds to the position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274 or 275 in SEQ ID NO. 1, assigned in an alignment with SEQ ID NO. 1, or that the amylase is modified at a position that corresponds to the position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484 or 485 in SEQ ID NO. 2, assigned in an alignment with SEQ ID NO. 2.

5. The method according to claim 1, wherein the component stabilizing the hydrolytic enzyme is comprised in an amount of 0.000001 to 10 wt % in the liquid preparation, and the hydrolytic enzyme is comprised in an amount of $1\times10^{-8}$ to 5 wt % in the liquid preparation relative to the total protein content of the hydrolytic enzyme.

6. The method according to claim 1, wherein the liquid preparation is a surfactant preparation.

7. The method according to claim 1, wherein the component stabilizing the hydrolytic enzyme comprises a compound that is selected from the group consisting of
   a) monosaccharide glycerate;
   b) oligoaminobiphenyl oligocarboxylic acids;
   c) aminophthalic acid;
   d) phthaloyl glutamic acid;
   e) polysubstituted benzoic acid that has a carboxyl group on at least two carbon atoms of the benzene ring;
   f) phenylalkyl dicarboxylic acids;
   g) glycerin, 1,2-ethylene glycol, 1,2-propylene glycol or 1,3-propylene glycol
   h) glyceric acid;
   i) calcium lactate or a lactate derivative;

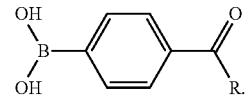

* * * * *